(12) United States Patent
Kuroda et al.

(10) Patent No.: US 7,776,525 B2
(45) Date of Patent: Aug. 17, 2010

(54) METHOD OF DIAGNOSING DISEASE RELATING TO ENDOMETRIOSIS

(75) Inventors: Masahiko Kuroda, Tokyo (JP); Kosuke Oikawa, Tokyo (JP); Yoshinori Kosugi, Tokyo (JP); Tetsuya Ohbayashi, Kyoto (JP)

(73) Assignee: Japanese Science and Technology Agency, Saitama (JP)

( * ) Notice: Subject to any disclaimer, the term of this patent is extended or adjusted under 35 U.S.C. 154(b) by 0 days.

(21) Appl. No.: 10/564,481

(22) PCT Filed: Jan. 13, 2004

(86) PCT No.: PCT/JP2004/000159

§ 371 (c)(1),
(2), (4) Date: Mar. 7, 2006

(87) PCT Pub. No.: WO2005/005983

PCT Pub. Date: Jan. 20, 2005

(65) Prior Publication Data

US 2007/0015160 A1   Jan. 18, 2007

(30) Foreign Application Priority Data

Jul. 14, 2003   (JP)  ............................. 2003-196455

(51) Int. Cl.
*C12Q 1/68*   (2006.01)
(52) U.S. Cl. ........................................................ 435/6
(58) Field of Classification Search ........................ None
See application file for complete search history.

(56) References Cited

U.S. PATENT DOCUMENTS

2001/0051344 A1* 12/2001 Shalon et al. .................. 435/6
2003/0172388 A1*  9/2003 Fujise et al. .................. 800/10

FOREIGN PATENT DOCUMENTS

WO       94/12881      6/1994
WO       02/22170      3/2002

OTHER PUBLICATIONS

Oikawa K, Ohbayashi T, Mimura J, Fujii-Kuriyama Y, Teshima S, Rokutan K, Mukai K, Kuroda M. Biochem Biophys Res Commun. Jan 25, 2002;290(3):984-7.*
Oikawa, et al. Increased expression of IgE-dependent histamine-releasing factor in endometriotic implants. J Pathol. Mar. 2003;199(3):318-23.*
Cheung (Cheung et al. Nature Genetics Mar. 2003; 33:422-425.*
Pepe et al. (American Journal of Epidemiology 2004 Vol. 159 p. 882).*

* cited by examiner

*Primary Examiner*—Sarae Bausch
*Assistant Examiner*—Katherine Salmon
(74) *Attorney, Agent, or Firm*—Wenderoth, Lind & Ponack, L.L.P.

(57) ABSTRACT

The expression level of a histamine-releasing factor (HRF) polynucleotide in a biological sample of a subject is measured and the HRF polynucleotide content is compared with that of a normal biological sample. An HRF polynucleotide expression level considerably higher than that of the normal biological sample is employed as an indication of a disease relating to endometriosis or a risk thereof.

4 Claims, 4 Drawing Sheets

Fig. 2
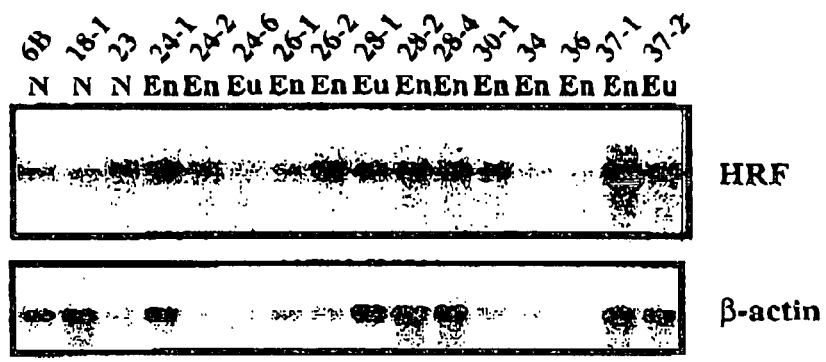
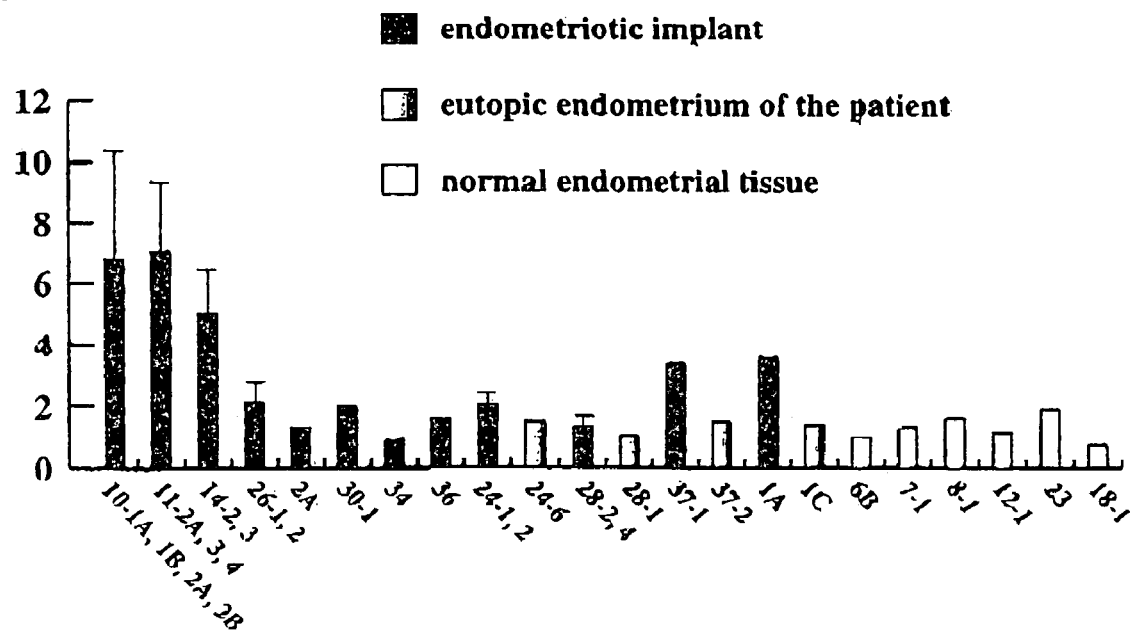

Fig.3
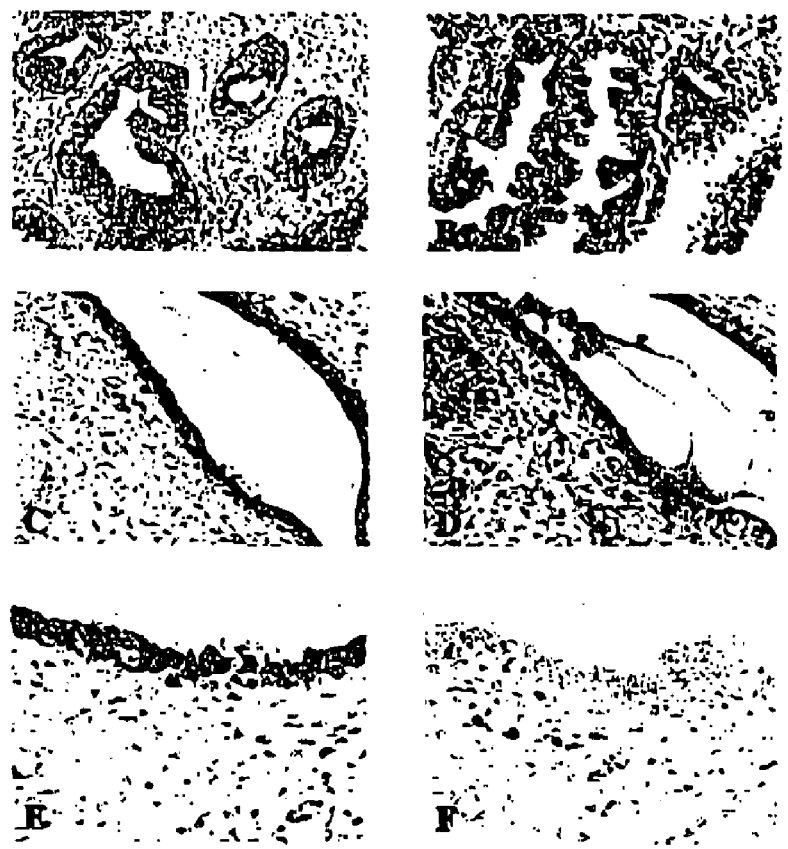
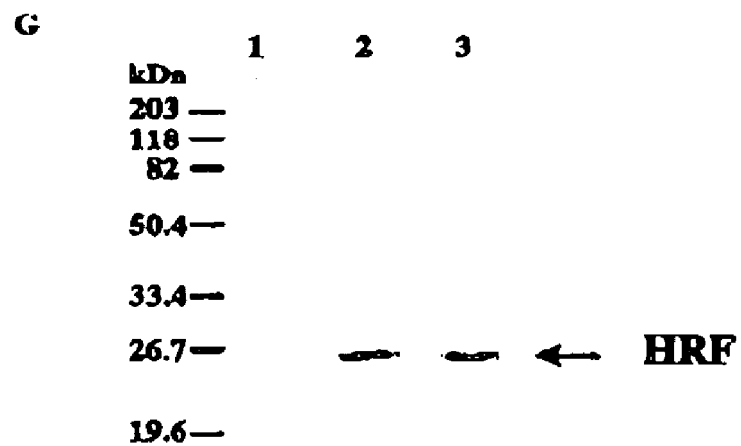

Fig. 4
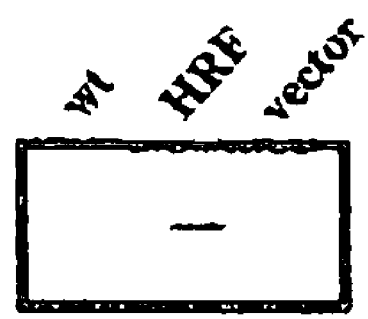
A
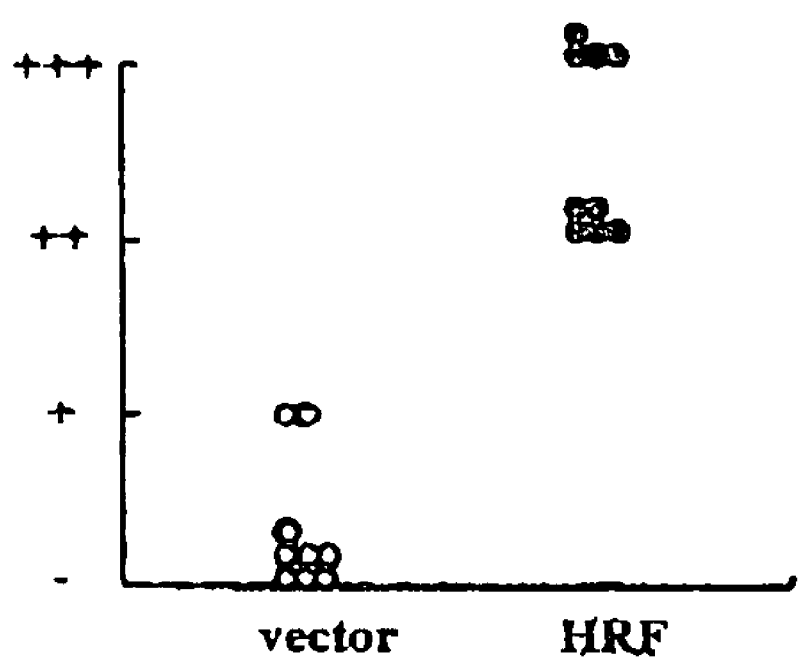
B

METHOD OF DIAGNOSING DISEASE RELATING TO ENDOMETRIOSIS

TECHNICAL FIELD

The present invention relates to a molecular biological method for diagnosing an endometriosis-related disease. The invention also relates to a therapeutic agent and a method for treating the relevant disease utilizing a molecular mechanism of an endometriosis-related disease.

BACKGROUND ART

An endometriosis is a common disease in an obstetric and gynecologic field, and manifested in 10% of all females at an age capable of reproduction (non-patent reference 1). A tissues of an endometriosis leads via a periodic proliferation and degradation similarly to a eutopic endometrium to a periodic dysmenorrhea, dyspareunia, pelvic pain and menstrual erythrocyturia. In addition, 30 to 40% of infertility patients are reported to have such a disease (non-patent reference 2). While a mechanism by which an endometrial cell is migrated and then proliferated locally in some of the patients is still unknown, it is possible that the de-regulation of an inflammatory cytokine is responsible for the advancement of an endometriosis (non-patent reference 3, 4). In fact, activation and migration into a peritoneum of a monocyte is one of the immunological abnormalities reported most consistently in the endometriosis (non-patent references 5 to 8).

A dioxin is one of endocrine disturbing substances and exists ubiquitously in an environment. 3,3,7,8-Tetrachlorodibenzo-p-dioxisin (TCDD; dioxin) is a substance having a highest toxicity among the dioxins, and exhibits various toxic effects (for example, immunotoxicity, hematotoxicity, teratogenicity, oncogenicity and the like) (non-patent references 9, 10). A change in a gene expression induced by TCDD and related compounds is initiated at the time point of the binding of a toxin to an allyl hydrocarbon receptor (AhR), and then a dimer with an allyl hydrocarbon receptor nuclear translocator (ARNT) is formed and a complex capable of interacting with a gene regulation element containing an XRE (xenobiotic responsive element) motif (non-patent references 11, 12). Since when a monkey was exposed chronically to TCDD a mild to severe endometriosis was developed dose-dependently (non-patent reference 13), several studies have been made on the relationship between a dioxin and an endometriosis (non-patent references 14 to 18). On the other hand, a recent report taught that a TCDD exposure is not correlated with an endometriosis (non-patent references 19, 20), and the relationship between the dioxin exposure and the endometriosis still remains unclear.

Applicants have identified a TCDD target gene including an IgE-dependent histamine releasing factor (HRF) (non-patent references 21 to 23). Nevertheless, no relationship has been suggested been such an HRF as a TCDD target gene product and the endometriosis.

Non-patent reference 1: Wheeler J. M. J. Reprod Med. 1989, 34(1):41-6
Non-patent reference 2: Candiani G. B. et al., Obstct Gynecol. Surv. 1991, 46(6):374-82
Non-patent reference 3: Garcia-Velasco J. A. and Arici A. Fertil Steril. 1999, 71(6):983-93
Non-patent reference 4: Barcz et al., Med. Sci. Monit. 2000, 6(5):1042-6
Non-patent reference 5: Jolicoeur C. et al., Am. J. Pathol. 1998, 152(1): 125-33
Non-patent reference 6: Lebovic D. I. et al., Fertil Steril 2001, 75(1):1-10
Non-patent reference 7: Hornung D. et al., Am. J. Pathol. 2001, 158(6):1949-54
Non-patent reference 8: Blumenthal R. D. et al., Am. J. Pathol. 2000, 156(5): 1581-8
Non-patent reference 9: Chapman D. E. and Schiller C. M. Toxicol Appl. Pharmacol. 1985, 78(1):147-57
Non-patent reference 10: McGregor D. B. et al., Environ Health Perspect. 1998, 106 Suppl. 2:755-60
Non-patent reference 11: Sagawa K. and Fujii-Kuriyama T. J. Biochem. (Tokyo) 1997, 122(6):1075-9
Non-patent reference 12: Nebert D. W. Crit. Rev. Toxicol. 1989, 20(3):153-74
Non-patent reference 13: Rier S. E. et al., Fundam. Appl. Toxicol. 1993, 21(4):433-41
Non-patent reference 14: Gibbsons A. Science 1993, 262 (5183): 1373
Non-patent reference 15: Obsteen K. G. and Sierra-Rivera E. Endocrinol. 1997, 15(3):301-8
Non-patent reference 16: Bruner-Tran K. L. et al. Gynecol. Obstet. Invest. 1999, 48 Suppl. 1:45-56
Non-patent reference 17: Johson K. L. et al., Environ Health Perspect 1997, 105(7):750-5
Non-patent reference 18: Yang J. Z. and Foster W. G. Toxicol. Ind. Health 1997, 13(1):15-25
Non-patent reference 19: Igarashi T. et al., Endocr. J. 1999, 46(6):765-72
Non-patent reference 20: Pauwels A. et al., Hum. Reprod. 2001, 16(10):2050-5
Non-patent reference 21: Oikawa K. et al., Cancer Res. 2001, 61(15):5707-9
Non-patent reference 22: Oikawa K. et al., Biochem. Biophys. Res. Commun. 2002, 290(3):984-7
Non-patent reference 23: Ohbayashi et al., FEBS Lett. 2001, 508(3):341-4

DISCLOSURE OF INVENTION

There has conventionally existed no effective methods for diagnosing an endometriosis except for an invasive method using an intraperitoneal endoscope.

On the other hand, a molecular biological diagnosis using as an index a marker a protein specific to any of various human diseases or its gene expression is becoming common. Since this method requires no large-scale facility and poses a reduced burden on a subject to be tested, it can be conducted widely also in subjects having no particular subjective symptoms. Nevertheless, in a case of an endometriosis, there is no known marker protein or its gene which is effective for conducting such a molecular biological diagnosis.

The invention is based on such a circumstance described above, and its objective is to provide a molecular biological method utilizing a gene expression related closely to an endometriosis.

Another objective of the invention is to provide various materials employed in this diagnostic method.

For achieving the objectives descried above, the invention provides the following (1) to (11).

(1) A method for diagnosing an endometriosis-related disease which comprises measuring an expression level of histamine releasing factor (HRF) polynucleotide in a biological sampled from a subject, comparing the HRF polynucleotide expression level with that in a normal biological sample, and judging a subject exhibiting a significantly higher HRF polynucleotide expression level when compared with the normal biological sample as a patient having the endometriosis-related disease or as a subject at a high risk thereof.

(2) HRF oligonucleotide which hybridizes under a stringent condition with HRF polynucleotide.

(3) An oligonucleotide prove, which is a labeled HRF oligonucleotide of the invention (2).

(4) A DNA microarray having as a target capture probe the HRF oligonucleotide of the invention (2) or an HRF polynucleotide.

(5) A primer set for PCR amplification of an HRF polynucleotide.

(6) A method for diagnosing an endometriosis-related disease comprising at least the following steps:

(a) a step for preparing RNA from a biological sample of a subject;

(b) a step for subjecting the RNA prepared in the step (a) to an electrophoretic separation;

(c) a step for hybridizing the RNA prepared in the step (b) with the oligonucleotide probe of the invention (3) under a stringent condition;

(d) a step for comparing the signal level of the oligonucleotide probe which had been hybridized with the RNA in the step (c) as an index of the HRF polynucleotide expression level with a result of a normal biological sample; and, (e) a step for using a significantly higher HRF polynucleotide expression level when compared with the normal biologics sample as a index reflecting the degree of the endometriosis-related disease or a risk thereof.

(7) A method for diagnosing an endometriosis-related disease comprising at least the following steps;

(a) a step for preparing RNA from a biological sample of a subject;

(b) a step for preparing a labeled cDNA from the RNA prepared in the step (a);

(c) a step for contacting the labeled cDNA prepared in the step (b) with the DNA microarray of the invention (4);

(d) a step for comparing the signal level of the labeled cDNA which had been hybridized with a capture probe of the DNA microarray in the step (c) as an index of the HRF polynucleotide expression level with a result of a normal biological sample; and, (e) a step for using a significantly higher HRF polynucleotide expression level when compared with the normal biological sample as a index reflecting the degree of the endometriosis-related disease or a risk thereof.

(8) A method for diagnosing an endometriosis-related disease comprising at least the following steps:

(a) a step for preparing RNA from a biological sample of a subject;

(b) a step for synthesizing a cDNA using the primer set of the invention (5) with the RNA prepared in the step (a) as a template;

(c) a step for comparing the level of the cDNA prepared in the step (b) as a HRF polynucleotide expression index with a result of a normal biological sample; and, (d) a step for using a significantly higher HRF polynucleotide expression level when compared with the normal biological sample as a index reflecting the degree of the endometriosis-related disease or a risk thereof.

(9) A method for diagnosing an endometriosis-related disease comprising 2 or more diagnostic methods selected from the diagnostic methods according to the inventions (6), (7) and (8).

(10) A therapeutic agent for an endometriosis-related disease comprising a molecule which inhibits the expression of a intracellular HRF polynucleotide.

(11) A method for treating an endometriosis-related disease comprising administering a molecule which inhibits the expression of an intracellular HRF polynucleotide.

Thus, the inventors of the present invention investigated the expression of a TCDD target gene (HRF, CYP1A1) in an endometrial tissue and an endometriosis implant, and as a result discovered a high correlation between the advancement of the endometriosis and the HRF expression level, thus establishing the invention.

As used herein, the term "endometriosis-related disease" means an endometriosis and diseases caused by the endometriosis such as dysmenorrhea, infertility, adenomyosis uteri and the like. The term "diagnosis" means a judgment whether a subject is suffering from an endometriosis-related disease, a judgment whether there is any risk of developing an endometriosis-related disease in future, and a judgment whether there is any risk of recurrence of the endometriosis-related disease once after the treatment is completed. The diagnosis also includes measuring the degree at which a subject is suffering from, or at a risk of an endometriosis-related disease.

The term "HRF polynucleotide" means a molecule formed by binding an HRF protein-encoding polynucleotide [a phosphoric acid ester of a nucleoside of a purine or pyrimidine bound via a β-N-glycoside bonding to a sugar (ATP, GTP, CTP, UTP; or dATP, dGTP, dCTP, dTTP)]. Typically, it may be an HRF protein encoding genomic DNA, an mRNA transcribed from the genomic DNA, a cDNA synthesized from the mRNA. It may be a single strand or double strand. Those also included are a sense strand and an antisense strand of these genomic DNA, mRNA and cDNA. The term "polynucleotide" means a molecule having 100 or more nucleotides, while the term "oligonucleotide" means a molecule having 2 to 99 nucleotides. The terms "protein" and "peptide" means a molecule constituted from a plural of amino acid residues binding to each other via amide bonds (peptide bonds). Especially, one having 2 to 33 amino acid residues may be referred to as an "oligopeptide", while one having 34 or more may be referred to as a "polypeptide".

Any of the base sequences as well as the amino acid sequences in Sequence Listing encompasses those undergoing addition, deletion of one or more base or substitution by another base, as well as those undergoing addition, deletion of one or more amino acids or substitution by another amino acid.

Other terms and concepts in the invention are specified in more detail in the description of the embodiment and the examples of the invention. Basically, the terms are in accordance with the IUPAC-IUB Commission on Biochemical Nomenclature, and are also based on the meanings of the terms employed customarily in this field. In addition, various technologies employed for practicing this invention can readily and surely be conducted by those skilled in the art referring to the publications and the like. For example, it is possible to conduct the preparation of an agent in accordance with the method described in Remington's Pharmaceutical Sciences, 18th Edition, ed. A. Gennaro, Mack Publishing Co., Easton, Pa., 1990, and also to conduct the genetic engineering and molecular biological technologies in accordance with the methods described in J. Sambrook, E. F. Fritsch & T. Maniatis, "Molecular Cloning: A. Laboratory Manual (2nd edition)", Cold Spring Harbor Laboratory Press, Cold Spring Harbor N.Y. (1989); D. M. Glover et al., ed., "DNA Cloning", 2nd ed., Vol. 1 to 4, (The Practical Approach Series), IRL Press, Oxford University Press (1995); Ausubel, F. M. et al., Current Protocols in Molecular Biology, John Wiley & Sons, New York, N.Y., 1995; NIPPON SEIKAGAKUKAI, ed., "ZOKUSEIKAGAKUJIKKENKOZA 1, IDENSHIKEN-KYUHO II", TOKYO KAGAKU DOJIN 1986); NIPPON SEIKAGAKUKAI, ed., "SHINSEIKAGAKUJIKKEN-KOZA 2, KAKUSAN III (KUMIKAE DNA GIJUTSU)", TOKYO KAGAKU DOJIN 1992); R. Wu ed., "Methods in Enzymology", Vol. 68 (Recombinant DNA), Academic Press, New York (1980); R. Wu et al. ed., "Methods in Enzymology", Vol. 100 (Recombinant DNA, Part B) & 101 (Recombinant DNA, Part C), Academic Press, New York (1983); R. Wu et al. ed., "Methods in Enzymology", Vol. 153 (Recombinant DNA, Part D), 154 (Recombinant DNA, Part E) & 155 (Recombinant DNA, Part F), Academic Press, New York (1987); J. H. Miller ed., "Methods in Enzymology", Vol. 204, Academic Press, New York (1991); R. Wu et al. ed., "Methods in Enzymology", Vol. 218, Academic Press, New York (1993); S. Weissman (ed.), "Methods in Enzymology", Vol. 303, Academic Press, New York (1999); J. C. Glorioso et al., (ed) "Methods in Enzymology", Vol. 306, Academic Press, New York (1999) and the like including the methods described in the literatures cited therein as well as the methods substantially similar thereto or the methods modified therefrom (incorporated herein by reference).

BRIEF DESCRIPTION OF DRAWINGS

FIG. 2 shows the results of the examination of the HRF expressions in an endometriosis implant. (A) shows the results of the northern blotting analysis of the HRF expressions in a normal endometrium tissue, a eutopic endometrium tissue from an endometriosis patient and an endometriosis implant. The blot was subjected to a re-probing using a human β actin probe to determine a total RNA level. N, Eu and En on the column represent the normal endometrium tissue, the eutopic endometrium tissue from an endometriosis patient and the endometriosis implant, respectively. (B) shows a graph of the HRF mRNA levels measured by a northern blotting analysis of the samples examined in FIG. 1 and FIG. 2A. The HRF mRNA level was normalized for the β actin signal using a densitometry (MOLECULAR IMAGER, Nippon Bio-Rad). The mRNA level of the sample 6B is designated as 1 for convenience. When a plural of samples were derived from a single individual, a mean value was calculated and indicated. An error bar represents a maximum level among the plural of the samples.

FIG. 3 shows the results of an immunohistochemical analysis of the HRF and CD68 expressions. A brown color staining served as a visualization of a positive part. A counter staining employed a hematoxylin. (A) and (B) represent an HRF protein detection in a normal endometrial tissue (A: growth phase, B: secretion phase, original magnification ×200). (C) represents an HRF protein detection in an endometriosis implant in an ovary (original magnification ×200). (D) represents an hematoxylin-eosin staining of a continuous section showing the morphology of the endometriosis implant (original magnification ×200). (E) represents the HRF protein detection of the vision of (C) at a higher magnification (original magnification ×400). (F) represents an immunohistochemical localization of a CD68-positive macrophage in the endometriosis implant (original magnification ×400).

FIG. 4 shows the results of an implantation assay. (A) shows the results of a western blotting analysis of an HRF protein in an NIH3T3 cell. wt: Parent NIH3T3 cell, HRF: a cell line (pMSCV-HRF-3T3) which expresses an HRF stably after infection with an HRF-containing retrovirus vector, vector: a control cell (pMSCV-3T3) infected with an empty vector. (B) shows a high implantation efficiency of an HRF-overexpressing cell in a nude mouse. Marks on an ordinate represent the followings: +++: numerous implantation colonies are observed, ++: several ten implantation colonies are observed, +: several implantation colonies are observed, −: no implantation colonies are observed. An individual mouse received the injection of the control cell or the HRF-overexpressing cell is indicated by open circle or solid circle.

BEST MODE FOR CARRYING OUT THE INVENTION

Figure 1:
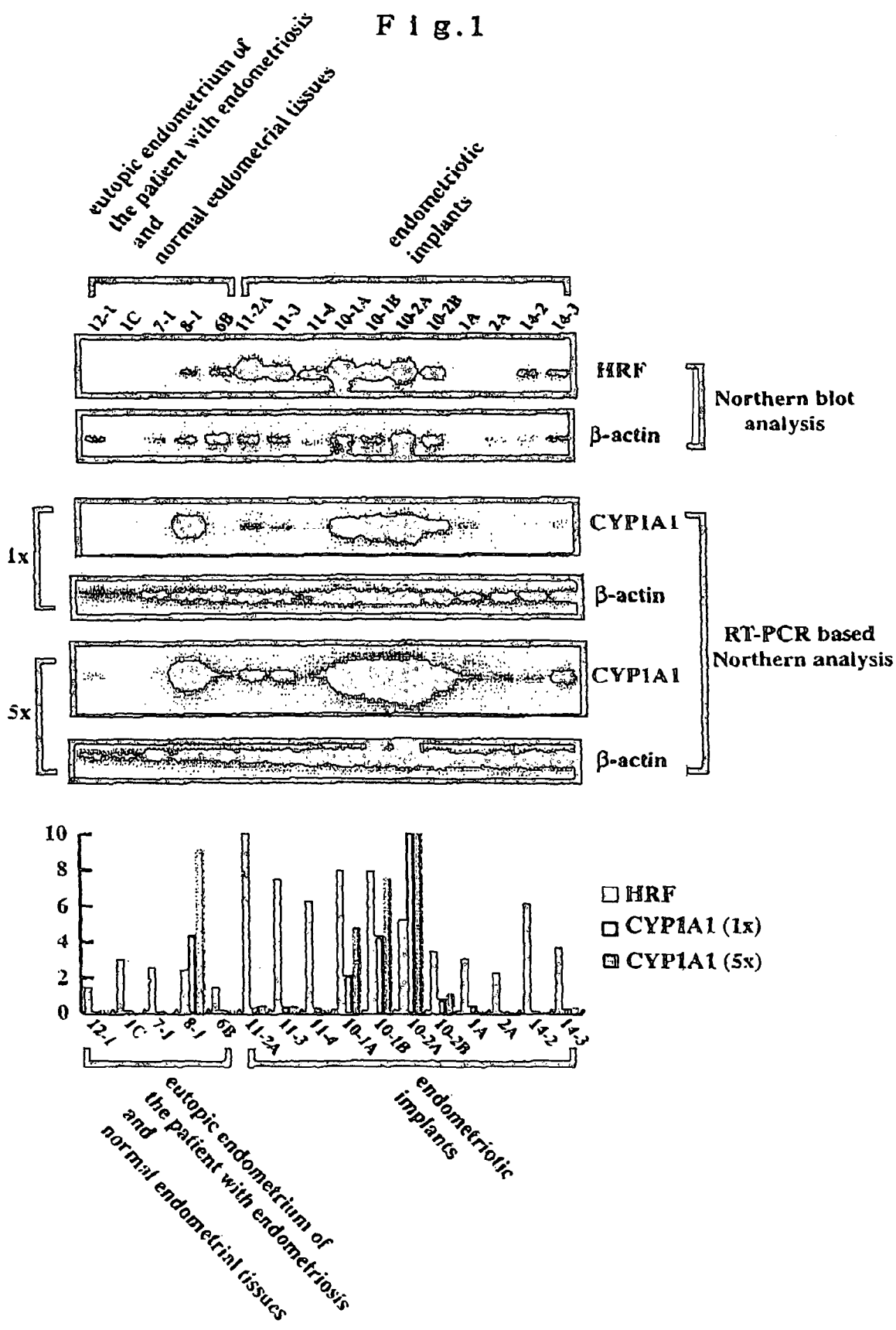
FIG. 1 shows the result of the examination of the expressions of an HRF and a CYP1A1 in a eutopic endometrium tissue from an endometriosis patient as well as an endometriosis implant. The top portion shows an HRF mRNA level was measured by a northern blotting analysis. The blot was subjected to a re-probing using a human β actin probe to determine a total RNA level. A CYP1A1 mRNA level in a sample examined by the northern blotting was determined by a quantitative RT-PCR using a southern blotting analysis. In order to verify the quantification accuracy, cDNA samples at concentrations of a 5-fold difference (1× and 5×) were employed as PCR templates and examined in a similar layout. A β actin was used as an internal standard for the mRNA level. The bottom portion shows an image display for the HRF and CYP1A1 mRNA levels is shown similarly. An mRNA level was normalized for the β actin signal using a densitometry (MOLECULAR IMAGER, Nippon Bio-Rad). The sample 11-2A exhibits an HRF mRNA level, while the sample 10-2A exhibits a CYP1A1 mRNA level, which are designated as 10 for convenience. When a plural of samples were derived from a single individual, a mean value was calculated and indicated. An error bar represents a maximum level among the plural of the samples. 12-1, 7-1, 8-1 and 6B correspond to normal endometrial tissues, while IC designated with asterisk corresponds to a eutopic endometrium of an endometriosis patient.

A diagnostic method of the invention (1) is a method in which an HRF polynucleotide expression level in a biological sample from a subject is measured and then this HRF polynucleotide expression level is employed as an index to diagnose an endometriosis-related disease. Thus, a subject exhibiting a significantly higher HRF polynucleotide expression level when compared with the normal biological sample is judged as a patient having the endometriosis-related disease or as a subject at a high risk thereof. Since an HRF polynucleotide expression level is related closely to an endometriosis-related disease, this HRF polynucleotide expression level in a biological sample (for example menstrual blood) of a subject can be used as an index to diagnose the endometriosis-related disease. In addition, the phrase "significantly higher" HRF polynucleotide expression level means that an HRF polynucleotide expression level in a subject is higher by 10% or more, preferably 30% or more, more preferably 70% or more, most preferably 100% or more, when compared with a normal biological sample (i.e. a biological sample from a normal healthy individual). Furthermore, this phrase "significantly higher" means that for example when a mean of the HRF polynucleotide expression levels in a plural of biological samples from a single identical subject and a similar mean in a plural normal samples are tested statistically the former is greater significantly than the latter.

While a number of HRF polynucleotide variants are known (for example, GenBank/XM_294045, XM_038391, XM_293291, XM_209741, XM_210566, XM_066706, XM_066675, XM_071321 and the like), a preferred one may for example be HRF cDNA (or TPT-1; GenBank/NM_003295) represented by SEQ ID. No. 1 (base sequence). Such a polynucleotide can readily be obtained each by a known method. For example, in the case of a cDNA, a known method (Mol. Cell Biol. 2, 161-170, 1982; J. Gene 25, 263-269, 1983; Gene, 150, 243-250, 1994) may be employed to synthesize a cDNA library and a probe DNA prepared each based on known base sequence may be employed to isolate a respective cDNA. The cDNA thus obtained can be amplified by a standard gene amplification method such as a PCR (polymerase chain reaction) method, NASBN (nucleic acid sequence based amplification) method, TMA (transcription-mediated amplification) method and an SDA (strand displacement Amplification) method and the like. Also it is possible to obtain a required amount of each cDNA by an RT-PCR using as a template a mRNA isolated from a human cell using a primer set provided by the invention.

As mentioned above, a diagnostic method according to the invention (1) using an HRF polynucleotide expression level at an index can be conducted by detecting and measuring the HRF polynucleotide expression level by a method known in the art for detecting End measuring a particular gene, including an in situ hybridization, northern blotting, dot blotting, RNase protection assay, RT-PCR, Real-Time PCR (Journal of Molecular Endocrinology, 25, 169-193 (2000) and references cited therein), DNA array analysis method (Mark Shena ed., "Microarray Biochip Technology", Eaton Publishing, March, 2000) and the like. An of the HRF polynucleotide expression level measurement system, an endometriosis-related disease detection system, endometriosis-related disease risk detection system, reagents, methods, processes, analytical programs utilized therein, which employ the technologies listed above, are encompassed by the inventive technologies as well as the systems utilizing the same.

The invention provides especially the following inventions (2) to (5) as materials employed in a diagnostic method of the invention (1).

An HRF oligonucleotide of the invention (2) is characterized in that it hybridizes under a stringent condition with an HRF polynucleotide.

This HRF oligonucleotide can also be obtained for example by cleaving the HRF oligonucleotide described above (cDNA) with a suitable restriction enzyme. Alternatively, it can be synthesized in vitro by a chemical synthesis technology known per se such as those described for example in Carruthers (1982) Cold Spring Harbor Symp. Quant. Biol. 47:411-418; Adams (1983) J. Am. Chem. Soc., 105:661; Belousov (1997) Nucleic Acid Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

A stringent condition means a condition which enables a selective and detectable specific binding between a polynucleotide and an oligonucleotide described above. A stringent condition is defined by salt concentrations, organic solvent (for example, formamide), temperature and other known parameters. Thus, the stringency is increase by reducing the salt concentration, by increasing the organic solvent concentration or by elevating the hybridization temperature. For example, a stringent salt concentration is usually about 750 mM NaCl or less and about 75 mM trisodium citrate or less, more preferably, about 500 mM NaCl or less and about 50 mM trisodium citrate or less, most preferably, about 250 mM NaCl or less and about 25 mM trisodium citrate or less. A stringent organic solvent concentration is about 35% formamide or more, most preferably about 50% or more. A stringent temperature condition is bout 30° C. or higher, higher preferably about 37° C. or higher, most preferably about 42° C. or higher. Other parameters include hybridization period, detergent (for example, SDS) concentration, presence or absence of a carrier DNA, and these parameters may be combined as appropriate to achieve any of various stringency levels. In a preferred embodiment, a hybridization is conducted with 750 mM NaCl, 75 mM trisodium citrate and 1% SDS at 30° C. In a more preferred embodiment, a hybridization is conducted with 500 mM NaCl, 50 mM trisodium citrate, 1% SDS, 35% formamide, 100 µg/ml denatured salmon sperm DNA at 37° C. In a most preferred embodiment, a hybridization is conducted with 250 mM NaCl, 25 mM trisodium citrate, 1% SDS, 50% formamide, 200 µg/ml denatured salmon sperm DNA at 42° C. The condition under which a washing is conducted after the hybridization also influence on the stringency. This washing condition is defined also by salt concentrations and temperature, and the stringency is increased by reducing the salt concentrations and elevating the temperature. For example, a stringent salt condition for a washing is preferably about 30 mM NaCl or less and about 3 mM trisodium citrate or less, most preferably, about 15 mM NaCl or less and about 1.5 mM trisodium citrate or less. A stringent temperature condition for a washing is about 25° C. or higher, more preferably, about 42° C. or higher, and most preferably, about 68° C. or higher. In a preferred embodiment, a washing is conducted with 30 mM NaCl, 3 mM trisodium citrate and 0.1% SDS at 25° C. In a more preferred embodiment, a washing is conducted with 15 mM NaCl, 1.5 mM trisodium citrate and 0.1% SDS at 42° C. In a most preferred, embodiment, a washing is conducted with 15 mM NaCl, 1.5 mM trisodium citrate and 0.1% SDS at 68° C.

The invention (3) is an oligonucleotide obtained by labeling an HRF oligonucleotide described above. The labeling can be conducted by a radioisotope (RI) method or a non-RI method, with the non-RI method being preferred. Such a non-RI method may for example be a fluorescent labeling method, biotin labeling method, chemilumunescent method and the like, with a fluorescent labeling method being preferred. A fluorescent substance may any one capable of binding to a base moiety of an oligonucleotide, and those which can be employed are cyanine dyes (for example, Cy Dye™ series, Cy3, Cy5 and the like), rhodamine 6G reagent, N-acetoxy-$N^2$-acetylaminofluorene (AAF), AAIF (iodinated derivative of AAF) and the like. As a labeling method, any method known in the art (for example, random priming method, nick translation method amplification of a DNA by a PCR method, labeling/tailing method, in vitro transcription method and the like) can appropriately be selected and employed. For example, a functional group (for example, a primary aliphatic amino group, SH group) is introduced into an HRF oligonucleotide and to such a functional group a label described above is bound to produce a labeled oligonucleotide probe.

The invention (4) is a DNA microarray having as a target capture probe an HRF oligonucleotide or an HRF polynucleotide of the invention (2) described above.

As methods for producing microarrays, a method for synthesizing an oligonucleotide directly on a solid phase support (on-chip method) and a method for immobilizing on a solid phase support surface an oligonucleotide or a polynucleotide which has previously bees prepared are known. A microarray employed in the invention can be produced by any of these methods. An on-chip method can be conducted for example by combining the use of a protective group capable of being cleaved selectively by a light irradiation with a photolithographic technology employed in a semiconductor production and a solid phase synthesis technology whereby effecting a selective synthesis at a certain region in a very little matrix (masking technology: for example, Fodor, S. P. A. Science 251:767, 1991). On the other hand, when an oligonucleotide or a polynucleotide which has previously been prepared is immobilized on a solid phase support surface, an oligonucleotide to which a functional group has been introduced is synthesized and the oligonucleotide is deposited on the surface of a solid phase support whose surface has been treated whereby effecting a covalent bonding (for example, Lamture, J. B. et al., Nucl. Acids Res. 42:2121-2125, 1994; Guo, Z. et al., Nucl. Acids Res. 22:5456-5465, 1994). Generally, the oligonucleotide and the polynucleotide are bound covalently via at spacer or crosslinker to the solid phase support whose surface has been treated. A method is also known in which a microparticle of a polyacrylamide gel is aligned on a glass surface where a synthetic oligonucleotide is then bound covalently (Yershov, G. et al., Proc. Natl. Acad. Sci. USA 94:4913, 1996). In another known method, an array of fine electrodes is ma de on a silica microarray and a penetration layer of a streptoavidin-containing agarose is formed on an electrode to yield a reaction site, and this site is charged positively to allow a biotinylated oligonucleotide to be immobilized while controlling the charge on the site whereby enabling a fast and accurate hybridization (Sosnowski, R. G. et al., Proc. Natl. Acad. Sci. USA 94:1119-1123, 1997). When this microarray is employed to diagnose an angitis, a cDNA is synthesized for example using a mRNA isolated from a cell of a subject and then amplified by a PCR. During this process, a labeled dNTP is incorporated to obtain a labeled cDNA. This cDNA is brought into contact with the microarray, and a cDNA which has been hybridized with a capture probe (oligonucleotide or polynucleotide) of the microarray is then detected. The hybridization can be conducted by dispensing the labeled cDNA aqueous solution into a 96- or 384-well plastic plate followed by deposition onto the microarray. The amount to be deposited may be about 1 to 100 nl. The hybridization is conducted preferably at room temperature to 70° C. for a period of 6 to 20 hours. After completing the hybridization, a mixture of a surfactant and a buffer solution is used to wash any unreacted labeled cDNA off. It is preferable to use sodium dodecyl sulfate (SDS) as a surfactant. While a buffer solution may for example be a citrate buffer, phosphate buffer, borate buffer, tris buffer, Good's buffer and the like, it is preferred to use a citrate buffer.

The invention (5) is a primer set for subjecting an HRF polynucleotide to a PCR amplification. This primer may be designed based on a known base sequence and prepared through respective steps for synthesis and purification. Care must be taken for example as described below upon preparing the primers. The primer size (number of bases) is 15 to 40 bases, preferably 15 to 30 bases for a satisfactory specific annealing with a template DNA. Nevertheless, at least 30 bases are effective when conducting an LA (long accurate) PCR. In order to avoid any mutual annealing within a combination or a pair (2 strands) consisting of a sense strand (5' end) and an antisense strand (3' end), a complementary sequence between the both primers should be avoided while also avoiding a self-complementary sequence for preventing any hairpin structure within a primer. In addition, for the purpose of ensuring a stable binding with the template DNA, the GC content should be about 50%, whereby avoiding any localization of GC-rich or AT-rich region within a primer. Since the annealing temperature depends on Tm (melting temperature), primers having Tms which are close to each other at 55 to 65° C. should be selected for the purpose of obtaining a highly specific PCR product. It should also be ensured to adjust the final concentration of a primer used in the PCR at about 0.1 to about 1 µM. It is a so possible to use a commercially available primer designing software, for example Oligo™ (National Bioscience Inc., (United States)), GENETYX (SOFTWARE KAIHATSU (KK), (JAPAN)) and the like.

By using the materials described above (the inventions (2) to (5)), it becomes possible to produce a reagent set for diagnosing various forms of an endometriosis-related disease and a risk thereof and also to construct a diagnostic method. Especially in this invention, the following inventions (6) to (9) are provided as methods for diagnosing endometriosis-related diseases and risks thereof.

Thus, a diagnostic method of the invention (6) is a method for detecting an HRF polynucleotide expression level (mRNA level) using the oligonucleotide of the invention (3) (northern blotting method). This diagnostic method comprises at least the following steps:

(a) a step for preparing RNA from a biological sample of a subject;

(b) a step for subjecting the RNA prepared in the step (a) to an electrophoretic separation;

(c) a step for hybridizing the RNA prepared in the step (b) with the oligonucleotide probe of the invention (3) under a stringent condition;

(d) a step for comparing the signal level of the oligonucleotide probe which had been hybridized with the RNA in the step (c) as an index of the HRF polynucleotide expression level with a result of a normal biological sample; and, (e) a step for using a significantly higher HRF polynucleotide expression level when compared with the normal biological sample as a index reflecting the degree of the endometriosis-related disease or a risk thereof.

A diagnostic method of the invention (7) is a method employing a DNA microarray of the invention (4). This diagnostic method comprises at least the following steps:

(a) a step for preparing RNA from a biological sample of a subject;

(b) a step for preparing a labeled cDNA from the RNA prepared in the step (a);

(c) a step for contacting the labeled cDNA prepared in the step (b) with the DNA microarray of the invention (4);

(d) a step for comparing the signal level of the labeled cDNA which had been hybridized with a capture probe of the DNA microarray in the step (c) as an index of the HRF polynucleotide expression level with a result of a normal biological sample; and, (e) a step for using a significantly higher HRF polynucleotide expression level when compared with the normal biological sample as a index reflecting the degree of the endometriosis-related disease or a risk thereof.

A diagnostic method of the invention (8) is a method for detecting an HRF polynucleotide (typically mRNA) expression level using a primer set of the invention (5) (RT-PCR method). This diagnostic method comprises at least the following steps;

(a) a step for preparing RNA from a biological sample of a subject;

(b) a step for synthesizing a cDNA using the primer set of the invention (5) with the RNA prepared in the step (a) as a template;

(c) a step for comparing the level of the cDNA prepared in the step (b) as a HRF polynucleotide expression index with a result of a normal biological sample; and, (d) a step for using a significantly higher HRF polynucleotide expression level when compared with the normal biological sample as a index reflecting the degree of the endometriosis-related disease or a risk thereof.

A diagnostic method of the invention (9) is a method comprising 2 or more diagnostic methods selected from the diagnostic methods of the above-mentioned inventions (6), (7) and (8).

A diagnostic method provided by this invention can be combined with a method for diagnosing an endometriosis-related disease in which an antibody capable of recognizing an HRF protein encoded by an HRF polynucleotide is employed to measure the level of the HRF protein.

In each of the diagnostic method described above, the observation of a label or the quantification of the label can employ, depending on the type of the label, any method known in the art appropriately such as a method employing a dark-field microscope, phase-contrast microscope, reflection-contrast microscope, fluorescent microscope, digital imaging microscope, electron microscope and the like.

The diagnostic methods described above are useful in diagnosing, preventing and treating an endometriosis-related disease. Moreover, they are useful after the treatment of the endometriosis-related disease, i.e., in knowing a prognosis.

The invention (10) is a therapeutic agent for an endometriosis-related disease comprising a molecule which inhibits the expression of an intracellular HRF polynucleotide, and the invention (11) is a method for treating an endometriosis-related disease comprising administering a molecule which inhibits the expression of an intracellular HRF polynucleotide. Thus, as shown also in the following Examples, since a cell overexpressing an HRF polynucleotide proliferates in vivo extensively, it is possible that the intracellular HRF polynucleotide overexpression causes an endometrial tissue implantation or proliferation. Accordingly, by suppressing the expression of this HRF polynucleotide it becomes possible to treat an endometriosis-related disease, or, at least arrest or suppress the advancement or the exacerbation of the disease.

A molecular suppressing the intracellular HRF polynucleotide expression may for example be an antisense sequence, ribozyme, chimera oligo, RNA interference (RNAi)-inducing double strand RNA molecule and the like (hereinafter all referred to as "expression-suppressing molecule"). The RNAi is preferred especially since it is a method which allows an exogenous RNA molecule to degrade an mRNA of a target gene whereby suppressing the expression of the target gene and thus it has a far more excellent target gene expression-suppressing effect when compared with an antisense sequence and the like. An RNA molecule employed may for example be a double strand RNA (dsRNA), more preferably a short chain (about 20 to 25 bp) RNA thereof (small interfering RNA:siRNA) (for example, Elbashir S. M. et al., Genes Dev. 2001, 15(2):188-200), a hairpin structure short chain RNA (short hairpin RNA:shRNA) (for example, Paddison P. J. et al., Genes Dev. 2002, 16(8):948-958) and a short chain RNA other than siRNA (small temporally regulated RNA: stRNA) (for example, Grosshans H. and Slack F. J., J. Cell Biol. 2002, 156(1):17-21) and the like.

As described above, an expression-suppressing molecule is designed based on the sequence of a target gene (HRF polynucleotide) (for example SEQ ID No.1), and can be prepared by a known method such as a chemical synthesis or an in vitro transcription. It is proposed that care must be taken as described below upon designing an siRNA. (1) 5' and 3' UTR regions and a region around an initiation codon where there are many regulatory protein-binding sites are excluded; (2) a region 50 to 100 nucleotide downstream of the initiation codon is selected (3) a region which is AA(N19)TT or AA(21) from the selected region having a GC content at least 30% to 70%, preferably about 50% is selected.

While an expression-suppressing molecule thus prepared may be administered to a body in a mixture with a suitable solvent, it is administered preferably in a form of an expression vector for the purpose of a sustained efficacy. Such an expression vector may be a plasmid vector or viral vector and the like. For example, a plasmid vector for expressing an RNA molecule for an RNAi may be a commercially available piGENE series, pSINsi/pBAsi series and the like. A viral vector may for example be an adenovirus which is replication deficient, or which can replicate under a certain condition or which is modified to be replication competent (for example, human adenovirus genome-derived replication non-competent vector, see, for example, U.S. Pat. Nos. 6,096,718; 6,110,458; 6,113,913; 5,631,236), an adeno-associated virus and a retrovirus genome-derived vector. A retrovirus vector here may for example be one whose main ingredient is a mouse leukemia virus (MuLV), a gibbon ape leukemia virus (GaLV), a simian immunodeficiency virus (SIV), a human immunodeficiency virus (HIV), as well as a combination thereof (see, for example, U.S. Pat. Nos. 6,117,681; 6,107,478; 5,658,775; 5,449,614; Buchscher (1992) J. Virol. 66:2731-2739; Johann (1992) J. Virol. 66:1635-1640). Such a retrovirus, for example in the case of an adenovirus for an siRNA expression, can be prepared in a manner in which a base plasmid vector (for example pBAsi) is first constructed and from this base vector a promoter+an siRNA-encoding sequence is cut out and integrated into an adenovirus vector-producing cosmid, which recombinant cosmid is then transfected into a 293 cell and the like.

An expression vector as described above can be administered to a body via various route including patient's endometrium according to a standard gene therapy procedure. When using a plasmid vector, an intravenous administration by a hydrodynamic method (Song E. et al., Nature Medicine, 2003, 9(3):347-351) is also preferred.

EXAMPLES

The invention is further detailed and specified by the Examples shown below, which are not intended to restrict the invention in any way.

1. Materials and Methods 1-1. Tissue Samples

For RNA preparation, the following samples were obtained from 18 patients. 1) Endometriosis implants (n=21), 2)

Eutopic endometrium tissues from endometriosis patients (via curage, n=4), 3) Normal endometrial tissues from patients having no endometriosis (n=6). Several samples were obtained from different sites of a single individual. A sample was frozen in a liquid nitrogen, stored at −80° C. prior to the RNA preparation. An endometriosis implant was obtained from an ovary. Samples having normal endometrial tissues for the RNA preparation and endometrial tissues exhibiting normal proliferation and secretion, obtained via formalin fixation and paraffin embedding, were from patients having smooth muscle tumors and prolapse of the uterus. Pathological specimens were graded by a histological examination, and the results indicated that they were distributed over the range from Grade III to Grade IV of an endometriosis (t-ASRM: revised. American Society for Reproductive Medicine classification of endometriosis, 1996). The female subjects in this study exhibited no endometrial hyperplasia or tumor formation, and did not receive preoperative anti-inflammatory agents or hormone agents. Informed consents were obtained before the surgery in accordance with a protocol approved by an in-facility audit committee regarding to human body inspection in Tokyo Medical University Hospital.

1-2. Northern Blotting Analysis

A northern blotting was conducted as described in a reference (Oikawa K. et al., Cancer Res. 2001, 61(15):5707-9). An HRF probe was prepared as described in a reference (Oikawa K. et al., Biochem. Biophys. Res. Commun. 2002, 290(3): 984-7). A human β actin cDNA control probe (CLONTECH Laboratories, Inc.) was employed as a standard.

1-3. RT-PCR Using Southern Blotting

As described in a reference (Kubota M. et al., Am. J. Pathol. 1997, 151(3):735-44), the first strand cDNA was produced from a total RNA using oligonucleotide dT primers. Then, 2 μl (1×) and 10 μl (5×) of the resultant first strand cDNA solution were employed as a template to conduct the PCR. After adding four primers shown below, the initial denaturation was conducted at 95° C. for 2 minutes, followed by 22 cycles of 95° C. for 0.5 minutes, 65° C. for 0.5 minutes and 72° C. for 1 minute, where by amplifying CYP1A1 and β actin cDNA fragments, CYP1A1 amplification primers:

5'-ccacaaccaccaagaactgcttag-3' (SEQ ID No.3)

5'-gaaggggacgaaggaagagtg-3' (SEQ ID No.4)

β actin amplification primers:

5'-gggaaatcgtgcgtgacgttaag-3' (SEQ ID No.5)

5'-tgtgttggcgtacaggtctttg-3' (SEQ ID No.6)

After fractionating the amplification products by an electrophoresis on an agarose gel, a blotting and a hybridization were. Conducted. The CYP1A1 cDNA probe was obtained by a reverse transcription PCR using the primers described above. A human β actin cDNA probe (CLONTECH) was employed as a control. These cDNA probes were labeled with 32P using Rediprime II random trime labeling system (Amersham Pharmacia Biotech).

1-4. Antibody Preparation and Immunohistochemical Method

A peptide antibody against a human HRF-derived oligopeptide (GKLEEQRPERVKPFMT: 101 to 116 of SEQ ID No.2) was prepared in accordance with a standard method using a rabbit and designated as an HRF-GKL. An immunohistochemical analysis was conducted by incubating a section made free of the paraffin in the presence of a mixture solution of an anti-HRF antibody, an HRF-TPY (Oikawa K. et al. Biochem. Biophys. Res. Commun. 2002, 290(3):984-7) and an HRF-GKL (diluted to 1:100) or an anti-human CD68 antibody (diluted to 1:100, Dako). For the anti-HRF staining, a section made free of the paraffin was subjected to a heat-induced antigen recovery using an autoclave. An LSABC (Dako) was used but here with 3,3'-diaminobentizine as a dye. A hematoxylin was employed for the counter staining.

1-5. Western Blotting Analysis

A western blotting analysis was conducted as described in a reference (Oikawa K. et al., Biochem. Biophys. Res. Commun. 2002, 290(3):984-7). A membrane probe treatment was conducted using an anti-HRF (HRF-GKL or HRF-TPY) antibody at 1:2000 dilution ratio. A signal was detected using an ECL plus Western blotting detection system (Amersham Pharmacia Biotech).

1-6. Cell Culture and Retrovirus Infection

An NIH3T3 cell was obtained from American Type Culture Collection (ATCC). The cell was maintained at 37° C. in a DMEM (GIBCO BRL, Life Technologies, Inc.) supplemented with 10% FBS under a 5% $CO_2$ atmosphere. A mouse HRF cDNA containing a full-length ORF was amplified by a PCR using the primers shown below.

5'-ttggatccatgatcatctaccgggacctg-3' (SEQ ID No.7)

5'-ttgaattcttaacatttctccatctctaa-3' (SEQ ID No.8)

A cDNA thus obtained was digested with BamHI and EcoRI and cloned into a BglII-EcoRI site of a retrovirus expression vector MSCV-puro (CLONTECH). The recombinant retrovirus preparation and infection protocol was in accordance with the description in a reference (Kuroda et al., Proc. Natl. Acad. Sci. USA 1999, 96(9):5025-30). 24 Hours after the infection, 1 μg/ml puromycin (CLONTECH) was employed to select the infected cells over 2 weeks.

1-7. Animal and Treatment

A partial specimen of $5 \times 10^5$ cells was injected intraperitoneally into a 6-week female BALB/C nude mouse to conduct an implantation assay. The animal was sacrificed after two weeks and the implant colonies were counted.

2. Results 2-1. TCDD-Induced Gene HRF Expression Pattern in Endometriosis

The HRF expression pattern during an endometriosis was determined by a northern blotting analysis. As a result, a high level HRF expression was observed in an endometriosis implant tissue obtained from 3 out of 5 patients (FIG. 1). Since a part of a human cytochrome p450 gene superfamily (for example, CYP1A1, CYP1A2 and CYP1B1) are induced by dioxin, the induction of the CYP1A1 will be a primary target for a dioxin-dependent gene expression regulation. Accordingly, the relationship between exposure to dioxin and HRF expression was examined by investigating the CYP1A1 expression using an RT-PCR by a southern analysis (Trifa Y. et al., J. Biol. Chem. 1998, 273(7):3980-5; Oikawa K. et al., Gene 2000, 261(2):221-8). As a result, it was revealed that the CYP1A1 was not induced in all cases exhibiting higher HRF expressions (FIG. 1). Accordingly, the HRF was proven to be induced in the endometriosis implant regardless of the TCDD exposure, in spite that it was possible that the HRF expression was induced by the TCDD in some cases.

2-2. HRF Overexpression in Endometriosis Implant

In an endometriosis implant of a patient developing an endometriosis additionally, the HRF was revealed to be expressed. Thus, 7 cases of the endometriosis were subjected to a northern blotting analysis (FIG. 2A). When comparing a normal endometrial tissue and a eutopic endometrium tissue from an endometriosis patient, a high HRF expression was observed in the endometriosis implant (FIG. 2B).

2-3. HRF Immunohistochemistry of Normal Endometrium and Endometriosis Implant

The endometrial cell type which expresses an HRF was determined by an immunohistochemistry using an anti-HRF polyclonal antibody. As a result, it was identified that the HRF existed in both of the endometrial gland and the normal tissue interstitial cell, while the endometrial gland exhibited a higher expression (FIGS. 3A and 3B). There was no marked change in the expression pattern between the secretion and proliferation phases. The HRF expression in the endometriosis implant was also investigated. As a result, the HRF existed in both of the interstitial and epithelial components in the endometriosis implant of an ovary (FIGS. 3C and 3E). While the HRF expression in the normal endometrial interstitial cell was weak, both of the endometrial gland and the interstitial cell of the ovarian endometriosis implant exhibited similarly high level HRF expressions. Such a specific signal to the HRF was not observed when using a pre-immunization serum as a control (data not shown). Nevertheless, the HRF induction mechanism in an endometriosis implant is still unclear. In consistent with the report that a macrophage induced an HRF at the stage of activation by M-CSF (Teshima S., et al, J. Immunol. 1998, 161(11):6353-66), the involvement of a CD68-positive macrophage in an endometriosis implant was observed (Hornung D. et al., Am. J. Pathol. 2001, 158(6): 1949-54). Accordingly, by utilizing a CD68 staining on a continuous section of the implant, a CD68-positive macrophage inside the HRF overexpression region was identified (FIG. 3F). A control section which was hematoxylin-eosin stained exhibited an overall morphology of an endometriosis implant section. Based on these results, the HRF production in the endometriosis implant was suspected to be contributed by the macrophage.

2-4. HRF Effect on Intraperitoneal Implantation of NIH3T3 Cell

A physiological effect of an increase HRF expression was investigated. The cause of an endometriosis is still unknown (Klninckx R. P. et al., Gynecol Obstet Invest. 1999, 47, Suppl. 1:3-9, discussion 9-10; van der Linden P. J. Q. Front Biosci. 1997, 2:c48-52). If agreeing with a major hypothesis, the onset of an endometriosis is due to implantation and proliferation of an endometrial tissue which reached to an abdominal cavity because of an oviduct backflow (retrograde menstruation). Here we investigated an effect of an HRF on this implantation. First, a stable transformant of an NIH3T3 cell which overexpresses the HRF was prepared. After infection with a retrovirus vector for the HRF expression (pMSCV-HRF), a high HRF expression was noted (FIG. 4A). Then, these cells were injected intraperitoneally to a nude mouse. The pMSV-HRF-3T3 cell had a higher implantation ability when compared with a cell infected with a control vector (pMSC-3T3) (FIG. 4B). Based on these data, an HRF is suggested to play an important role not only in an immunological dysfunction but also in an initial development of an endometriosis implant.

INDUSTRIAL APPLICABILITY

As detailed above, the invention provides a method for diagnosing an endometriosis-related disease and the risk thereof conveniently and reliably as well as materials used for the same. As a result, it becomes possible to identify an endometriosis-related disease at an earlier stage, to select a more appropriate therapeutic method and to prevent recurrence.

The invention claimed is:

1. A method for diagnosing endometriosis in a human, said method comprises:
   (a) measuring an expression level of histamine releasing factor (HRF) polynucleotide in a biological sample from a human subject wherein said biological sample is menstrual blood; and
   (b) comparing the HRF polynucleotide expression level with that in a normal biological sample, wherein a subject exhibiting a higher polynucleotide expression level when compared with the normal biological sample is indicative of a subject having endometriosis or a subject at risk thereof.

2. A method for diagnosing endometriosis in a human, said method comprising:
   (a) preparing RNA from a biological sample of a human subject, wherein said biological sample is menstrual blood;
   (b) subjecting the RNA prepared in step (a) to an electrophoretic separation;
   (c) hybridizing the RNA prepared in step (b) with a labeled HRF oligonucleotide probe that hybridizes under a stringent condition with HRF polynucleotide;
   (d) comparing the signal level of the labeled HRF oligonucleotide probe which hybridized with the RNA in step (c) as an index of the HRF polynucleotide expression level with a result of a normal biological sample; and,
   (e) using a higher HRF polynucleotide expression level when compared with the normal biological sample as a index reflecting, the degree of endometriosis or risk thereof.

3. A method for diagnosing endometriosis in a human, said method comprising:
   (a) preparing RNA from a biological sample of a human subject, wherein said biological sample is menstrual blood;
   (b) preparing a labeled cDNA from the RNA prepared in step (a);
   (c) contacting the labeled cDNA prepared in step (b) with a DNA microarray having as a target capture probe an HRF polynucleotide or an HRF oligonucleotide that hybridizes under a stringent condition with HRF polynucleotide;
   (d) comparing the signal level of the labeled cDNA which hybridized with the capture probe of the DNA microarray in step (c) as an index of the HRF polynucleotide expression level with a result of a normal biological sample; and,
   (e) using a higher HRF polynucleotide expression level when compared with the normal biological sample as a index reflecting, the degree of endometriosis or risk thereof.

4. A method for diagnosing endometriosis, said method comprising:
   (a) preparing RNA from a biological sample of a human subject, wherein said biological sample is menstrual blood;
   (b) synthesizing a cDNA using a primer set for PCR amplification of an HRF polynucleotide with the RNA prepared in step (a) as a template;
   (c) comparing the level of the cDNA prepared in step (b) as a HRF polynucleotide expression index with a result of a normal biological sample; and,
   (d) using a higher HRF polynucleotide expression level when compared with the normal biological sample as a index reflecting the degree of endometriosis or risk thereof.

* * * * *

SEQUENCE LISTING

<160> NUMBER OF SEQ ID NOS: 8

<210> SEQ ID NO 1
<211> LENGTH: 830
<212> TYPE: DNA
<213> ORGANISM: Homo sapiens
<220> FEATURE:
<221> NAME/KEY: CDS
<222> LOCATION: (95)..(613)

<400> SEQUENCE: 1

```
cccccccgag cgccgctccg gctgcaccgc gctcgctccg agtttcaggc tcgtgctaag      60
ctagcgccgt cgtcgtctcc cttcagtcgc catc atg att atc tac cgg gac ctc     115
                                     Met Ile Ile Tyr Arg Asp Leu
                                      1               5 atc agc cac gat gag atg ttc tcc gac atc tac aag atc cgg gag atc       163
Ile Ser His Asp Glu Met Phe Ser Asp Ile Tyr Lys Ile Arg Glu Ile
         10                  15                  20 gcg gac ggg ttg tgc ctg gag gtg gag ggg aag atg gtc agt agg aca       211
Ala Asp Gly Leu Cys Leu Glu Val Glu Gly Lys Met Val Ser Arg Thr
     25                  30                  35 gaa ggt aac att gat gac tcg ctc att ggt gga aat gcc tcc gct gaa       259
Glu Gly Asn Ile Asp Asp Ser Leu Ile Gly Gly Asn Ala Ser Ala Glu
 40                  45                  50                  55 ggc ccc gag ggc gaa ggt acc gaa agc aca gta atc act ggt gtc gat       307
```

```
Gly Pro Glu Gly Glu Gly Thr Glu Ser Thr Val Ile Thr Gly Val Asp
            60                  65                  70 att gtc atg aac cat cac ctg cag gaa aca agt ttc aca aaa gaa gcc      355
Ile Val Met Asn His His Leu Gln Glu Thr Ser Phe Thr Lys Glu Ala
        75                  80                  85 tac aag aag tac atc aaa gat tac atg aaa tca atc aaa ggg aaa ctt      403
Tyr Lys Lys Tyr Ile Lys Asp Tyr Met Lys Ser Ile Lys Gly Lys Leu
        90                  95                  100 gaa gaa cag aga cca gaa aga gta aaa cct ttt atg aca ggg gct gca      451
Glu Glu Gln Arg Pro Glu Arg Val Lys Pro Phe Met Thr Gly Ala Ala
    105                 110                 115 gaa caa atc aag cac atc ctt gct aat ttc aaa aac tac cag ttc ttt      499
Glu Gln Ile Lys His Ile Leu Ala Asn Phe Lys Asn Tyr Gln Phe Phe
120                 125                 130                 135 att ggt gaa aac atg aat cca gat ggc atg gtt gct cta ttg gac tac      547
Ile Gly Glu Asn Met Asn Pro Asp Gly Met Val Ala Leu Leu Asp Tyr
            140                 145                 150 cgt gag gat ggt gtg acc cca tat atg att ttc ttt aag gat ggt tta      595
Arg Glu Asp Gly Val Thr Pro Tyr Met Ile Phe Phe Lys Asp Gly Leu
                155                 160                 165 gaa atg gaa aaa tgt taa caaatgtggc aattattttg gatctatcac              643
Glu Met Glu Lys Cys
            170 ctgtcatcat aactggcttc tgcttgtcat ccacacaaca ccaggactta agacaaatgg     703 gactgatgtc atcttgagct cttcattat tttgactgtg atttatttgg agtggaggca      763 ttgttttta a gaaaaacatg tcatgtaggt tgtctaaaaa taaaatgcat ttaaactcat    823 ttgagag                                                              830

<210> SEQ ID NO 2
<211> LENGTH: 172
<212> TYPE: PRT
<213> ORGANISM: Homo sapiens

<400> SEQUENCE: 2

Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Asn Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170
```

```
<210> SEQ ID NO 3
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 3
ccacaaccac caagaactgc ttag                                              24

<210> SEQ ID NO 4
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 4
gaaggggacg aaggaagagt g                                                 21

<210> SEQ ID NO 5
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 5
gggaaatcgt gcgtgacgtt aag                                               23

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 6
tgtgttggcg tacaggtctt tg                                                22

<210> SEQ ID NO 7
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 7
ttggatccat gatcatctac cgggacctg                                         29

<210> SEQ ID NO 8
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 8
ttgaattctt aacatttctc catctctaa                                         29
```